United States Patent [19]

Gunther et al.

[11] Patent Number: 5,677,490
[45] Date of Patent: Oct. 14, 1997

[54] ULTRASONIC TESTING DEVICE FOR WELD SEAMS IN PIPES, SHEETS AND CONTAINERS

[75] Inventors: Werner Gunther, Pulheim; Bernhard Karbach, Erfstadt-Friesenheim; Helmut Heckhauser, Herne; Siegmar Schulz, Cologne, all of Germany

[73] Assignee: F. H. Gottfeld Gesellschaft fur Zerstorungsfreie Werkstoffprufung mbH, Germany

[21] Appl. No.: 505,339
[22] PCT Filed: Feb. 14, 1994
[86] PCT No.: PCT/DE94/00151
  § 371 Date: Feb. 16, 1996
  § 102(e) Date: Feb. 16, 1996
[87] PCT Pub. No.: WO94/19686
  PCT Pub. Date: Sep. 1, 1994

[30] Foreign Application Priority Data

Feb. 18, 1993 [DE] Germany ............ 43 04 952.4

[51] Int. Cl.⁶ .................. G01N 29/10; G01N 29/26
[52] U.S. Cl. ............... 73/622; 73/620; 73/624; 73/625; 73/628; 73/641
[58] Field of Search ................. 73/622, 628, 641, 73/625, 620, 624

[56] References Cited

U.S. PATENT DOCUMENTS

| | | | |
|---|---|---|---|
| 3,552,191 | 1/1971 | Heseding | 73/625 |
| 3,575,044 | 4/1971 | Gibbs et al. | 73/625 |
| 3,868,847 | 3/1975 | Gunkel | 73/622 |
| 3,958,451 | 5/1976 | Richardson | 73/622 |
| 4,170,145 | 10/1979 | Kennedy et al. | 73/620 |
| 4,375,165 | 3/1983 | de Sterke | 73/622 |
| 4,452,080 | 6/1984 | McFarland | 73/620 |
| 4,588,873 | 5/1986 | Fenn et al. | 73/598 |
| 4,744,250 | 5/1988 | Ganglbauer et al. | 73/588 |
| 5,111,696 | 5/1992 | Lund et al. | 73/627 |

OTHER PUBLICATIONS de Sterke, "Automatic ultrasonic inspection of pipeline welds", Dec. 1980, pp. 275–284.

*Primary Examiner*—Hezron E. Williams
*Assistant Examiner*—Nashmiya Ashraf
*Attorney, Agent, or Firm*—Carol I. Bordas; Noland J. Cheung

[57] ABSTRACT

The ultrasonic testing device for weld seams (28) in pipes, sheets and containers, preferably for circumferential welds in pipelines, is fitted with two identical test head supports (20), each fitted with at least one test head (e.g., 23), arranged in lateral inversion to the weld seam, which acoustically irradiate from the basic material (30) of the pipes or sheets laterally into the weld seam (28) and are coupled to the surface of the basic material (30) opposite the root (32) of the weld seam (28). Each test head support (20) has a plurality of immersion test heads (22-24) arranged one behind the other or side-by-side transversely to the weld seam (28) in such a way that their acoustic irradiation entry regions into the basic material (30) are as close together as possible and of which a) one immersion test head (22) is directed so that it generated a creeping wave in the basic material (30) on the side of the root (36) of the weld seam (28) which spreads out at the surface and of which b) at least two other immersion test heads (23, 24) irradiate at a flatter angle than the first-mentioned head (22) for longitudinal fault testing, and one of these immersion test heads (23) for longitudinal faults irradiates the weld seam (28) in the region of the root (32).

14 Claims, 2 Drawing Sheets

ULTRASONIC TESTING DEVICE FOR WELD SEAMS IN PIPES, SHEETS AND CONTAINERS

BACKGROUND OF THE INVENTION

1. Field of the Invention

The invention relates to an ultrasonic inspection system (testing device) for use in submerged arc welding lines (weld seams) in pipes and metal sheets, preferably panoramic lines of pipeline-pipes, with two inspection head supports of the same construction, which are specularly arranged to the weld line. Each inspection head support comprises at least one inspection head each, which sends a wave sideways from the base material of the pipes and metal sheets into the weld line. Each inspection head support is attached on the surface of the base material, positioned opposite of the root position of the weld line. This invention relates to hand as well as automatically welded lines, i.e, lines of containers.

2. Description of the Prior Art

An ultrasonic inspection system is known from the DE 4030893 A1. With this system, two angle-inspection heads are attached via crack coupling to the base material right and left of the weld line, and is measured through reciprocal acoustic irradiation.

U.S. Pat. No. 4,570,487 shows a process for inspecting cracks in bimetallic, coarse grained specimens. Thereby, a transmitting ultrasonic transducer emits into the specimen to be inspected in such a way that a creep or surface wave is formed on the surface of the specimen, which is opposite to the surface coupled to the transducer. At the crack, this creep wave converts to a volume wave if the crack extends to the surface of the specimen. The volume wave is received by the receiving ultrasonic transducer. During such an inspection, a weld seam in the vicinity of the crack would form a mechanical obstacle, if there is a mechanical deformation that obstructs the motion of the transducer.

U.S. Pat. No. 3,868,847 refers to a process and a device for the ultrasonic inspection of lengthy weld seams which have a central root, gap coupling is used. There is no use for surface waves.

DE-book "Werkstoffprufung mit Ultraschall" (Ultrasonic testing of materials), 1980, p. 475 to 477 and 490 to 500 reports about use of surface waves for testing resistance welded steel tubes. In the book, doubt is expressed whether surface waves or possibly Lamb or plate waves were used.

With the above-ultrasonic inspection system, only a sub-range step of the weld line is seized, unless the two inspection head supports are shifted back and forth synchronically diagonal to the weld line in such a way that a complete acoustic irradiation through the complete weld line is achieved. The synchronization of the two movements appears to be very difficult with the manually executed test as well as with the use of mechanical operating systems. On the other hand, the interpretation of echo indicators, especially the differentiation between flank and root indicators becomes difficult, because the error signals are gained via constantly changing points of wave-entrance. With mechanical operating mechanisms, the time input and electronic resources are extremely high, therefore, the error signals can only be gained via constantly changing wave entrance points. An automatic test is hard to realize with such a known inspection system.

SUMMARY OF THE INVENTION

This is where the invention steps in. It is the task of the invention to further develop the inspection system of the above-mentioned kind. This task is performed without relative motion of the inspection head supports diagonal to the weld line such that, the complete cross-section of the weld line can be seized with sufficient sensitivity and on the other hand, can be differentiated between binding and root errors, as well as the possibility of separate error echos from presentation echos.

The task is solved by departing from the inspection system of the above-mentioned kind in such a way that each inspection head support shows several immersion-technique inspection heads. The inspection heads are attached diagonally to the weld line in such a way, that their points of wave entrance into the base material are as close together as possible and can be adjusted definitely and of which a) one immersion-technique inspection head is projected in such a way that it produces a creep wave, expanding on the surface, in the base material on the surface, bordering directly on the root position of the weld line and of which b) at least two further immersion technique inspection heads for longitudinal error testing send waves in a flatter angle than the first mentioned immersion technique inspection head, where one of these immersion technique inspection heads for longitudinal errors sends acoustic irradiation through the weld line as close to the root position as possible.

Because of this solution, relative motions of the inspection heads support, which are diagonal to the weld line, are not necessary. Accordingly, a rough adjustment of the inspection heads to the geometrical center of the line is sufficient. As a result, the mechanical motion input on an axis and automatic test systems can be realized more simply and reproducably. Only when shifting the beam of the complete line a follow-up device of the complete test system takes place.

It is sufficient during an inspection to shift the inspection head supports together parallel to the course of the weld line with a weld line being situated between them. Due to that, the device according to the invention is better suited for inspection systems working automatically.

According to the invention, different wave shapes are worked with, to better and more securely seize the root position of the weld line. The root position in the areas close to the surface are tested by the immersion technique inspection head of each inspection head support, which are installed for creep waves inspection. By the inspection head for longitudinal error testing, which acoustically irradiates through the weld line in the area of the root position, possible reflectors are proven additionally and also the area connected to the testing, operated through creep waves is additionally tested. Here, a combination of the two test results is offered in a development for a secure statement concerning errors.

With the state of art, instead of angle inspection heads with crack coupling, immersion technique inspection heads are being used, since they possess a higher persistence of the spot. Furthermore, a more even sound-field distribution is realized in the material.

The individual immersion technique inspection heads are arranged as narrowly as possible next to each other, as the test task permits, such that, their point of wave entrance lies a closely as possible next to each other. The coupling via a water-flowing distance is relatively easy in operation. It is also sufficient for practical use, to control the orderly coupling of only one immersion technique inspection head in a special testing rhythm. If such inspection head is orderly coupled, it can be assumed that the other inspection head is orderly coupled via the water-flowing distance. By this, the test electronics is considerably simplified. For the coupling, only one mutual attached water connection is required.

Individual inspection heads can be used as inspection heads, but a linear array of inspection heads can also be used. The first solution has the advantage of having inspection heads that can be exchangeable and also individually adjustable. Defective inspection heads can easily be exchanged and the inspection head support can be equipped according to the special demands by choosing a number in accordance to the required task and by positioning the individually adjustable individual inspection heads. The second solution has the advantage, that the test density is greater and the array can also be operated as phased array, which allows a back and forth continual scanning by a swinging acoustic irradiation through the weld line.

In an improvement, an inspection head per test side for the inspection of longitudinal errors can be used, which is mechanically rotably arranged and which sweeps the required area of the wave entrance area by turning.

In another improvement, at least two further inspection heads for longitudinal error testing are projected parallel to each other. Without additional heads, at least two sound distances running parallel to each other are given in the base material, which penetrate the weld line at different points.

In a preferred embodiment, at least one additional immersion technique inspection head for each inspection head support for diagonal error testing is planned and arranged in such a way that its wave entrance area into the base material falls together as far as possible with the wave entrance areas of the other inspection heads. With this arrangement, the test area for the diagonal error testing is situated at another position of the weld line other than a simultaneously operating testing for longitudinal errors. But, as the difference is known, the testing is not made more difficult by this. But one gains the advantage that the coupling via the water-flowing distance does not need to be controlled separately.

In a preferred embodiment, the inspection heads for longitudinal errors are arranged on the line next to each other. This line may preferably run parallel to the weld line, but may be situated diagonal to it.

It has proven to be especially advantageous, if the errors, indicated by the creep waves inspection heads, are only taken into account in the evaluation, if the longitudinal error-inspection head, which sends waves through the root position, also shows an error at the same position. Normally, the sound intensity of creep waves depends on many factors and can vary from position to position. To ensure that no error is indicated by a feebly projected creep wave, reference occurs to the signal closest to the longitudinal error-inspection head. In this way, a secure statement with respect to errors is possible. Error is defined as "sound-unsounds", which is further defined as barriers of any kind in the normal sound (ultrasonic) propagation.

Finally, it has proven to be advantageous to also seize, besides the amplitudes when sending waves through and in the reflective mode of operation, the respective travel times, which are used to determine the position of the errors and to allow a further differentiation of error indicators.

In a further embodiment, the travel times of the form echos of the root are evaluated to have the inspection heads follow-up the course of the root.

Further advantages and characteristics of the invention result in the claims. The following illustrations of the embodiments are to be interpreted as illustrative and not in any limited sense as explained in reference to the drawings.

DESCRIPTION OF THE PREFERRED EMBODIMENT

Figure 1:
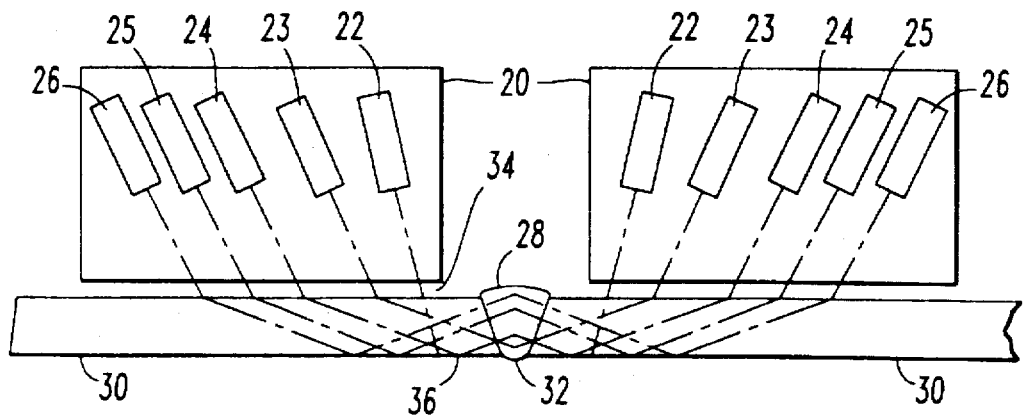
FIG. 1 is a side view of a left and right inspection head support with five (or six) inspection heads as well as a weld line with bordering base material areas and the central sound-beams.
Figure 2:
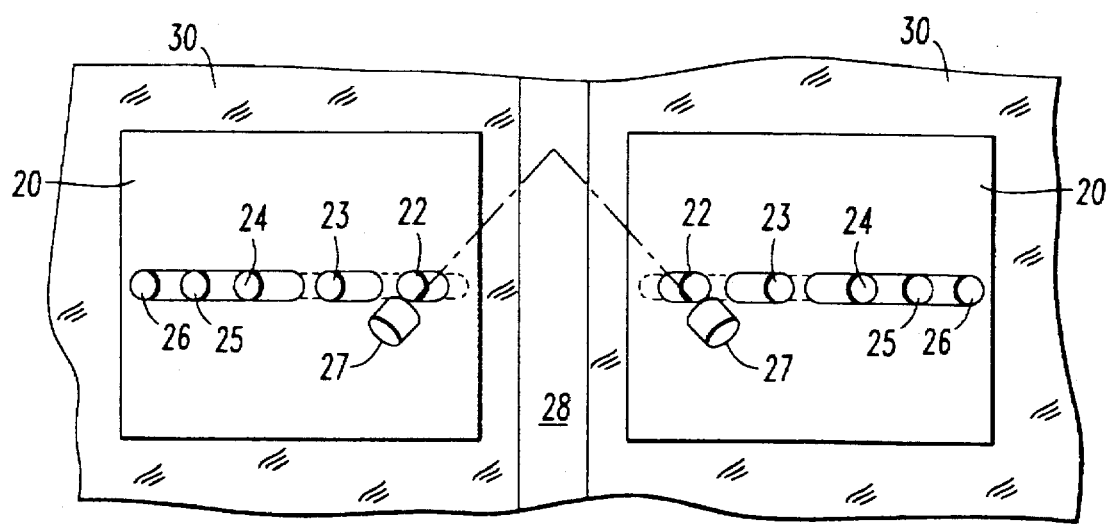
FIG. 2 is a top view of the arrangement according to FIG. 1.

The first embodiment according to FIG. 1 and FIG. 2 schematically shows two inspection head supports 20 of the same construction in which five inspection heads 22–26 are arranged. The two inspection head supports 20 are specularly arranged to the weld line 28, which stretches to the paper level in a right angle. To the right and to the left of the weld line 28, the areas of the base material 30 border the weld line 28. The weld line 28 is typically made by adding several weld levels, starting with a root level 32. Normally it has a V-shape cross-section, as shown in FIG. 1. With the inspection system, a complete inspection of the total cross-section area of the weld line 28 should be executed. In addition, the area at the V-top of this cross-section area should be securely seized. In this area, the inspection is difficult and often disturbed by form echos. In this area, error positions often occur.

The individual inspection heads 22–26 are immersion technique-inspection heads. They are coupled via a water-flowing distance 34 to the base material 30, acoustically, as hinted by the individual central-beams drawn in FIG. 1.

Inspection head 22 is closest to the weld line 28. It serves to produce indirect (secondary) creep waves, namely, the production of creep waves on the side of the root position 32 of the weld line 28. This process is performed by sending waves closer to the weld line 28 and in a steeper angle into the base material 30 than the other inspection heads 23–26. The inspection head 22 is arranged in an explicitly defined distance from the weld line 28, such that its sound-entrance possesses a given distance (i.e., about 20 mm) from it. As can be seen from FIG. 1, near the root position 32, a creep wave 36 is produced, which expands on the surface and sends waves through the weld line 28 in the area of its root position on the surface. It is taken up in a symmetrical arrangement by a respective inspection head 22 in the right inspection head support 20. The sound path has a U-shaped form. In another testing rhythm, the inspection head 22 of the right inspection head support 20 can be switched as sender and the inspection head 22 of the left inspection head support 20 can act as receiver.

Near the inspection head 22, there is a first inspection head 23 for the inspection of longitudinal errors. The first inspection head's 23 sound-entrance area into the base material 30 is situated in the direct vicinity of the sound-entrance area of inspection head 22. Due to the flatter sound entrance angle and the greater distance of the weld line 28, an essentially V-shaped sound path into the base material 30 and the weld line 28, is achieved, as shown in FIG. 1. The sound path runs as close as possible to the V-top of the cross-section of the weld line 28 such that, the root position 32 is seized. The inspection takes place near the inspection, which is operated by the secondary creep waves of the two inspection heads 22. By the correlation of the results of the inspection head pairs 22, 23, a far clearer statement about errors in the area of the root position 32 is achieved, as can be done according to the state of art.

The inspection head supports 20 of both sides possess a further three longitudinal error inspection heads 24–26, as well (FIG. 2) as an additional further inspection head 27 for diagonal errors. In the embodiment shown in FIG. 2, the inspection heads 24–26 stand parallel to the inspection head 23 and are positioned in a row behind each other such that, the arrangement in a row-like shape is projected diagonal to the longitudinal direction of the weld line 28. W-shaped sound distances in the base material 30 and the weld line 28 are achieved for the inspection heads 24–26, such that, the weld line 28 is inspected within the range over its entire cross-section.

The additional inspection head 27 for diagonal errors is arranged in such a way that it sends waves through the same water flowing distance 34 as the already discussed inspection heads 22–26. Because of that, the water-flowing distance chosen can be very small in space, as can be seen especially from FIG. 2, where it is drawn in a dotted illustration.

Figure 3:
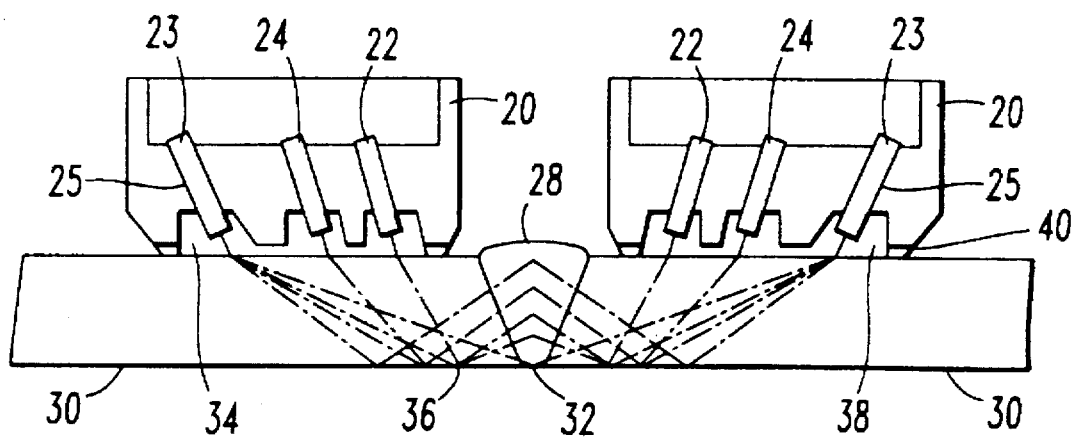
FIG. 3 is an illustration similar to FIG. 1 for another arrangement of inspection heads in an inspection head support.
Figure 4:
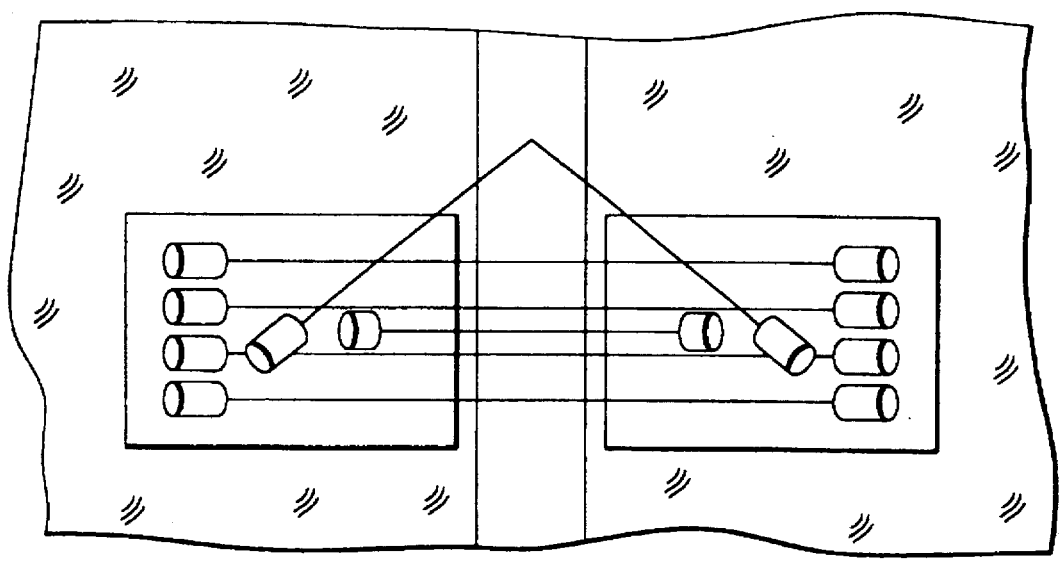
FIG. 4 is an illustration according to FIG. 2 for the embodiment according to FIG. 3.

The second embodiment, illustrated in FIGS. 3 and 4, is different from the first embodiment in general by the arrangement of the inspection heads 23–26 for longitudinal error inspection. These heads 23–26 are arranged in a row running parallel to the longitudinal direction of the weld line 28. The inspection head support 20 projects chambers 38 for the formation of the water-flowing distance 34. Altogether, there are three chambers 38 per inspection head support 20. The chambers 38 are connected with each other and are supplied with coupling liquid by a common, central connection (not illustrated). As FIG. 3 shows, the inspection heads 22–24 possess a slightly different inclination in comparison with each other, which leads to slightly different angles of incidence and to the differences shown in the angles of reflection.

In a preferred embodiment, the inspection heads 23–26 in the inspection head support angle can be adjusted spacially. The inspection head support 20 can be adjusted to the respective test task, especially to the thickness of the base material 30.

Around the chambers there are recoil-glide shoes 40, which prevent a side exit of the coupling liquid, such that and enormous amount of coupling liquid is saved. As such, recoil-glide shoes 40 or side sealing, ring-like rubber lips, plastic or metal frames or else can be used.

The nearly common point of ultrasound entrance of the inspection heads inside a water chamber, sending waves vertically and in an angle, additionally enables the control of the quality of the coupling by back wall monitoring of the inspection heads sending waves vertically. Instead of individual inspection heads, an inspection head array can be used. The running-time information of the root position can be evaluated and used for regulating the position of the inspection head system in a parallel way to the root. By electronic coupling the shield area to the echo-entrance changes in the difference of the water-flowing can be adjusted. The inspection head systems are diagonal to the line and are mechanically manageable to be able to follow the course of the line. The control signal for this is offered either via a line detection sensor or the running-time information of the root position.

We claim:

1. An ultrasonic testing device for testing a weld in a structure having a base material with a first surface and a second surface, wherein the weld has a weld line which extends substantially perpendicularly to the first and second surfaces and a root, said ultrasonic testing device comprising:

(a) two inspection head supports specularly arranged with respect to the weld;

(b) first inspection head means for transmitting and receiving ultrasonic radiation which enters the structure at the first surface and travels through the base material to the second surface, where the ultrasonic radiation takes the form of a creep wave, which propagates along the second surface and through the root wherein the creep wave engages the root in a direction which is substantially perpendicular to the weld line, and through the base material to the first surface wherein the creep wave is received by the first inspection head means such that the path of the ultrasonic radiation is substantially U-shaped, the first inspection head means is attached to the two inspection head supports and takes the form of immersion technique-inspection heads; and (c) second inspection head means for transmitting and receiving ultrasonic radiation which enters the structure at the first surface at a flatter entrance angle than the ultrasonic radiation of the first inspection head means, travels through the base material towards the second surface, through the root and back to the first surface such that the path of the ultrasonic radiation is substantially V-shaped, the second inspection head means is attached to the two inspection head supports and takes the form of immersion technique-inspection heads.

2. The ultrasonic testing device according to claim 1, wherein said first and second inspection head means are detachably secured to said two inspection head supports.

3. The ultrasonic testing device according to claim 1, wherein said first and second inspection head means are arranged angle-adjustably in said two inspection head supports.

4. The ultrasonic testing device according to claim 1, wherein said second inspection head means comprises at least four inspection heads for longitudinal error testing.

5. The ultrasonic testing device according to claim 4, wherein said second inspection head means for longitudinal error testing is arranged in one line which projects parallel to said weld line.

6. The ultrasonic testing device according to claim 1, further comprising at least one additional inspection head means in the form of an immersion technique inspection head to detect diagonal errors.

7. The ultrasonic testing device according to claim 1, further comprising at least one additional inspection head means for transmitting waves next to said weld line and vertically into said base material.

8. The ultrasonic testing device according to claim 1, wherein each of said two inspection head supports include a chamber, wherein said chambers are in connection with each other via a water flowing distance.

9. The ultrasonic testing device according to claim 8, wherein said chambers are connected with a mutual delivery pipe for coupling fluid.

10. The ultrasonic testing device according to claim 8, wherein said chambers being surrounded sideways by recoil-guide shoes for the reduction of side water loss.

11. The ultrasonic testing device according to claim 1, wherein said first and second inspection head means include both sending and receiving inspection heads.

12. The ultrasonic testing device according to claim 1, wherein a reflecting defect detected by the first inspection head means is taken into account for the evaluation of defects only if the second inspection head means also detects a reflecting defect.

13. The ultrasonic testing device according to claim 4, wherein said second inspection heads means for longitudinal error testing are arranged in one line which projects diagonal to said weld line.

14. The ultrasonic testing device according to claim 4, wherein the entry regions of the immersion technique-inspection heads of the first inspection head means and second inspection head means are at the first surface, and are as close together as possible.

* * * * *

UNITED STATES PATENT AND TRADEMARK OFFICE
CERTIFICATE OF CORRECTION

PATENT NO. : 5,677,490
DATED : October 14, 1997
INVENTOR(S) : Guenther, et al.

It is certified that error appears in the above-identified patent and that said Letters Patent is hereby corrected as shown below:

<u>Title page, item [73],</u>
After the first assignee add the following: -- and Krautkramer GmbH & Co. KG, --

Signed and Sealed this

Second Day of October, 2001

Attest:

*Nicholas P. Godici*

NICHOLAS P. GODICI
*Attesting Officer*     *Acting Director of the United States Patent and Trademark Office*